(12) United States Patent
Pu et al.

(10) Patent No.: US 8,515,529 B2
(45) Date of Patent: Aug. 20, 2013

(54) DETECTING SLEEP DISORDERS USING HEART ACTIVITY

(75) Inventors: Yachuan Pu, Dana Point, CA (US); Charles Gropper, Mission Viejo, CA (US); Dongping Lin, Irvine, CA (US)

(73) Assignee: Braemar Manufacturing, LLC, Eagan, MN (US)

( * ) Notice: Subject to any disclaimer, the term of this patent is extended or adjusted under 35 U.S.C. 154(b) by 256 days.

(21) Appl. No.: 12/370,090

(22) Filed: Feb. 12, 2009

(65) Prior Publication Data
US 2010/0204586 A1     Aug. 12, 2010

(51) Int. Cl.
*A61B 5/04*     (2006.01)

(52) U.S. Cl.
USPC .............................................. 600/509

(58) Field of Classification Search
USPC ................................. 600/509, 529
See application file for complete search history.

(56) References Cited

U.S. PATENT DOCUMENTS

| | | | |
|---|---|---|---|
| 4,958,641 A | 9/1990 | Digby et al. | |
| 4,977,899 A | 12/1990 | Digby et al. | |
| 5,191,891 A | 3/1993 | Righter | |
| 5,226,425 A | 7/1993 | Righter | |
| 5,522,396 A | 6/1996 | Langer et al. | |
| D377,983 S | 2/1997 | Sabri et al. | |
| 5,634,468 A | 6/1997 | Platt et al. | |
| 5,678,562 A | 10/1997 | Sellers | |
| 5,730,143 A | 3/1998 | Schwarzberg | |
| 5,931,791 A | 8/1999 | Saltzstein et al. | |
| D414,870 S | 10/1999 | Saltzstein et al. | |
| 5,966,692 A | 10/1999 | Langer et al. | |
| 6,102,856 A | 8/2000 | Groff et al. | |
| 6,126,611 A | 10/2000 | Bourgeois et al. | |
| 6,287,252 B1 | 9/2001 | Lugo | |
| 6,366,871 B1 | 4/2002 | Geva | |
| 6,574,507 B1 | 6/2003 | Bonnet | |
| 6,871,089 B2 | 3/2005 | Korzinov et al. | |

(Continued)

OTHER PUBLICATIONS

P. Stein et al., "Cyclic Variation in Heart Rate during Sleep in Four Recordings of up to 13 Years in Elderly Adults," Computers in Cardiology vol. 34, p. 33-35 (2007).

(Continued)

*Primary Examiner* — Carl H Layno
*Assistant Examiner* — Paula J Stice
(74) *Attorney, Agent, or Firm* — Ropes & Gray LLP

(57) ABSTRACT

Systems, methods, apparatus, and computer program products for detecting the existence of a sleep disorder in an individual using heart activity. In one aspect, machine-implemented methods include the actions of analyzing a machine-readable heart rate series of a monitored individual in the time domain using one or more digital data processing devices, detecting a cyclic variation in heart rate in the heart rate series as a result of the analysis in the time domain, and outputting, over an output, a report characterizing a sleep disorder event based on the detection of the cyclic variation in heart rate in the heart rate series. The cyclic variation in heart rate is indicative of a sleep disorder.

34 Claims, 10 Drawing Sheets

(56) References Cited

U.S. PATENT DOCUMENTS

| | | |
|---|---|---|
| 6,904,320 B2 | 6/2005 | Park et al. |
| 7,222,054 B2 | 5/2007 | Geva |
| 7,311,665 B2 | 12/2007 | Hawthorne et al. |
| 7,542,878 B2 | 6/2009 | Nanikashvili |
| 2002/0128804 A1 | 9/2002 | Geva |
| 2003/0055348 A1 | 3/2003 | Chazal et al. |
| 2003/0204213 A1* | 10/2003 | Jensen et al. ............. 607/17 |
| 2004/0010201 A1 | 1/2004 | Korzinov et al. |
| 2004/0176695 A1* | 9/2004 | Poezevara ............. 600/513 |
| 2005/0061315 A1 | 3/2005 | Lee et al. |
| 2005/0115561 A1 | 6/2005 | Stahmann et al. |
| 2005/0119711 A1 | 6/2005 | Cho et al. |
| 2005/0119833 A1 | 6/2005 | Nanikashvili |
| 2005/0203349 A1 | 9/2005 | Nanikashvili |
| 2006/0235315 A1 | 10/2006 | Akselrod et al. |
| 2007/0173728 A1 | 7/2007 | Pu et al. |

OTHER PUBLICATIONS

P. Stein et al. "Sleep Apnea Detection Using Sleep-Disordered Heart Rate in Implanted Devices," Presented at Associated Professional Sleep Societies (APSS) 23 pages ( 2005).

"SLEEP," vol. 28, Abstract Supplement, pp. A197, A198 (2005).

C. Guilleminault et al., "Cyclic Variation of Heart Rate in Sleep Apnoea Syndrome—Mechanism and Usefulness of 24h ECG as a Screening Technique," Lancet, pp. 126-131 (1984).

International Search Report issued in Application No. PCT/US2010/024070 on Aug. 17, 2010.

Biomedical Computer Laboratory, Institute for Biomedical Computing, Washington University, "Progress Report No. 21," Jul. 1, 1984-Jun. 30, 1985, 164 pages.

Savi Wireless—Mobile Cardiac Telemetry Brochure, published by at least May 2009, 12 Pages, Medicomp, Melbourne, Florida.

* cited by examiner

```
measure_score:
SCORE = -1; % Default value for each minute
% Score for each minute
if num >= 10 & f < 0.08 & f > 0.01 & sdHR>2 & mAmp > 10
    if sd < 0 | sd > 20
        ;
    elseif sd <= 6 & sdHR >= 2
        if sdHR >= 4
            SCORE = 100;
        elseif sdPkDist > 0 & sdPkDist <= 5
            SCORE = 100;
        elseif sdPkDist > 5 & sdPkDist <= 15
            SCORE = 90;
        elseif sdPkDist == -1
            SCORE = 80;
        end
    elseif sd <= 12 & sdHR >= 2
        if sdHR >= 4 & sdPkDist > 0 & sdPkDist <= 5
            SCORE = 100;
        elseif sdHR >= 4 & sdPkDist > 5 & sdPkDist <= 15
            SCORE = 90;
        elseif sdPkDist > 0 & sdPkDist <= 5
            SCORE = 80;
        elseif sdPkDist > 5 & sdPkDist <= 15 & f<0.04
            SCORE = 70;
        elseif sdPkDist == -1 & f<0.04
            SCORE = 60;
        end
    elseif sd <=18 & sdHR >= 2
        if sdPkDist > 0 & sdPkDist <= 5 & f<0.04
            SCORE = 90;
        elseif sdPkDist > 5 & sdPkDist <= 15 & f<0.04
            SCORE = 70;
        elseif sdPkDist == -1 & f<0.04
            SCORE = 50;
        end
    end
end
```

FIG. 4

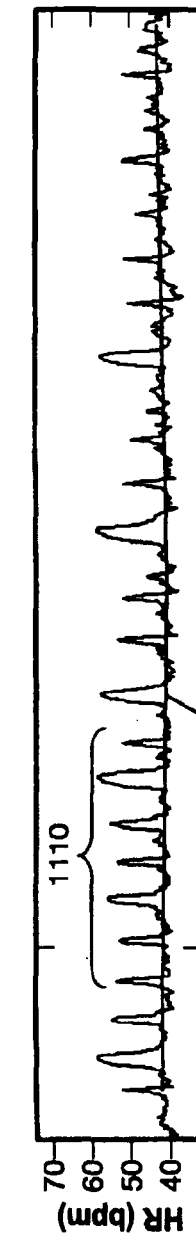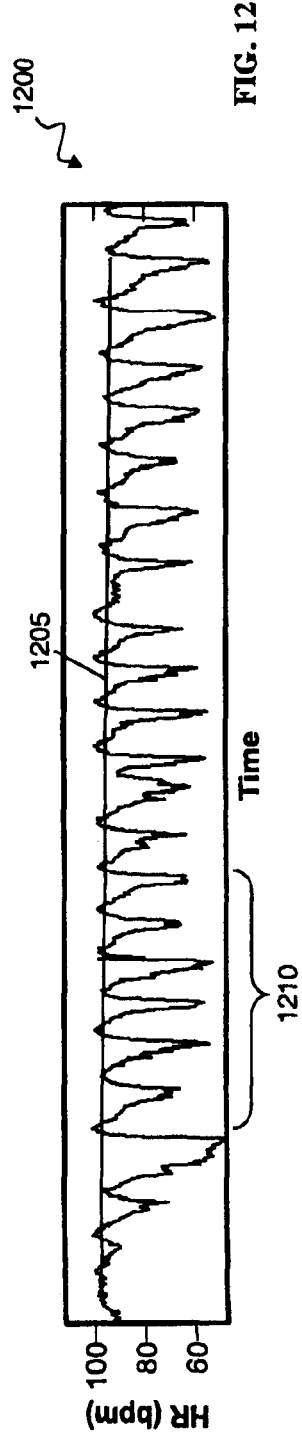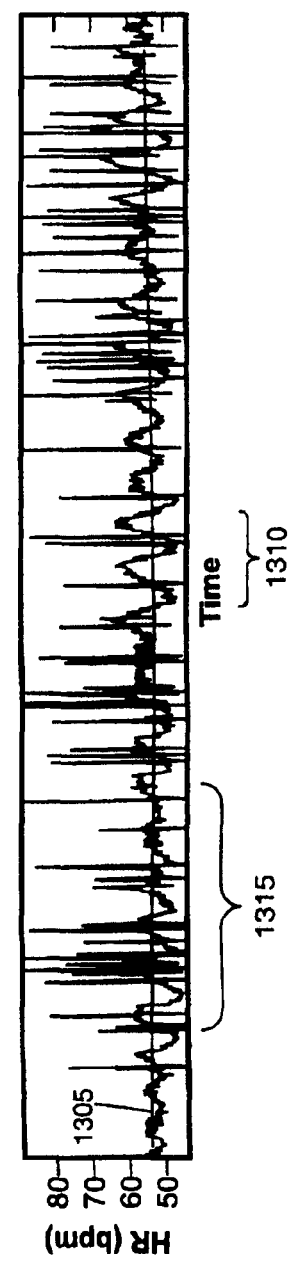

DETECTING SLEEP DISORDERS USING HEART ACTIVITY

BACKGROUND

This disclosure relates to detecting the existence of a sleep disorder in an individual using heart activity.

A sleep disorder is any of a group of syndromes characterized by disturbance in an individual's sleep, including, e.g., the amount of sleep, the quality or timing of sleep, or in behaviors or physiological conditions associated with sleep.

One class of sleep disorder is sleep apnea, which refers to sleep disorders that are characterized by pauses in breathing during sleep. Clinically significant sleep apnea can be associated with five or more pauses (i.e., five or more "apnea") per hour, with each individual pause lasting longer than 10 seconds. Sleep apnea can be associated with other physiological indicators, such as neurological arousals, blood oxygen desaturation, or combinations thereof.

One class of sleep apnea is obstructive sleep apnea (OSA). Obstructive sleep apnea is caused by physical obstruction of the airway that interrupts breathing despite an individual's effort to breathe. For example, in some forms of obstructive sleep apnea, soft tissue of the airway collapses to obstruct breathing as muscle tone relaxes during sleep.

Another class of sleep apnea is central sleep apnea. In contrast with obstructive sleep apnea, central sleep apnea is caused by a disorder of the central nervous system. For example, the nerve signals that trigger breathing can be delayed and an individual to miss one or more breathing cycles. If the pause in breathing is long enough, blood oxygen can drop and carbon dioxide can increase. In some instances, these conditions can trigger additional physiological effects, including nerve cell necrosis.

Another class of sleep disorder is Cheyne-Stokes respiration. In individuals suffering from Cheyne-Stokes respiration, breathing during sleep alternates between rapid and absent. Cheyne-Stokes respiration can be associated with heart failure, strokes, traumatic brain injuries, and brain tumors. In some instances, it can also occur during sleep at high altitudes, or as a result of toxic metabolic encephalopathy or carbon monoxide poisoning.

Another class of sleep disorder is periodic limb movement disorder, which is also referred to nocturnal myoclonus. In individuals suffering from periodic limb movement disorder, limbs are moved involuntarily during sleep to such an extent that the individual's sleep is disturbed. The movements, which occur in the legs more commonly than in the arms, generally occur for between 0.5 and 5 seconds and recur at intervals of between 5 and 90 seconds.

Polysomnography is a multi-parametric test that can be used to detect sleep apnea and other sleep disorders. During a typical polysomnography test, a variety of different aspects of the physiological condition of an individual are monitored. For example, the electrical activity of the brain (EEG), electrical activity associated with eye movements (EOG), electrical activity associated with other muscular activity or movements (EMG), the electrical activity of the heart (ECG), blood oxygen saturation (using, e.g., pulse oximetry), and movement of various parts of the body (e.g., the chest wall, the upper abdominal wall, the nose and nostrils, the chin, and/or the legs) can be monitored during polysomnography tests. Moreover, patients can be monitored visually by medical personnel during polysomnography tests.

SUMMARY

The present inventors have developed systems and techniques, including computer program products, for detecting of sleep disorders using heart activity. In some implementations, sleep disorders can be detected relying exclusively on heart activity. Indeed, detection of the existence of a sleep disorder using heart activity can be used to trigger the recording or transmission of measurements of other aspects of the physiological condition of a patient, as discussed further below.

In general, one aspect of the subject matter described in this specification can be embodied in apparatus that include one or more machine-readable data storage media storing instructions operable to cause one or more data processing machines to perform operations. The operations include receiving machine-readable heart rate information characterizing a heart rate of a monitored individual over a first interval, detecting at least one of bradycardia and a cyclic variation in heart rate in the heart rate information during the first interval, determining whether obstructive sleep apnea is indicated based at least on the detected at least one of bradycardia and cyclic variation in heart rate, and selectively reporting an obstructive sleep apnea event in response to the determination that sleep apnea is indicated. The obstructive sleep apnea event is a second interval when the information content of the received heart rate information is indicative of obstructive sleep apnea.

This and other aspects can include one or more of the following features. Measures of the cyclic variation in heart rate can be smoothed over a detection window to determine that obstructive sleep apnea is indicated. Information characterizing an aspect of the physiological condition of the monitored individual outside of the detection window can be reported. Information characterizing an aspect of the physiological condition of the monitored individual can be transmitted to a remote medical receiver. The information can include information characterizing aspects of the physiological condition of the monitored individual other than the heart.

Other embodiments of this aspect include corresponding systems, methods, and apparatus.

Another aspect of the subject matter described in this specification can be embodied in machine-implemented methods that include the actions of analyzing a machine-readable heart rate series of a monitored individual in the time domain using one or more digital data processing devices, detecting a cyclic variation in heart rate in the heart rate series as a result of the analysis in the time domain, and outputting, over an output, a report characterizing a sleep disorder event based on the detection of the cyclic variation in heart rate in the heart rate series. The cyclic variation in heart rate is indicative of a sleep disorder.

This and other aspects can include one or more of the following features. The methods can include one or more of establishing cyclic variation in heart rate indices from the heart rate series, establishing tachycardia indices from the heart rate series, and establishing bradycardia indices from the heart rate series.

The methods can also include determining that periodic limb movement sleep disorders are indicated based on tachycardia indices indicating that tachycardia is present, bradycardia indices indicating that bradycardia is not present, and cyclic variation in heart rate indices indicating that cyclic variation in heart rate is present. The methods can also include determining that obstructive sleep apneas are indicated based on tachycardia indices indicating that tachycardia is not present, bradycardia indices indicating that bradycardia is present, and cyclic variation in heart rate indices indicating that cyclic variation in heart rate is present. The methods can also include determining that repeated central apneas or Cheyne-Stokes respiration are indicated based on tachycardia indices indicating that tachycardia is present, bradycardia indices indicating that bradycardia is present, and cyclic variation in heart rate indices indicating that cyclic variation in heart rate is present. The methods can also include determining that repeated central apneas or Cheyne-Stokes respiration are indicated based on tachycardia indices indicating that tachycardia is not present, bradycardia indices indicating that bradycardia is not present, and cyclic variation in heart rate indices indicating that cyclic variation in heart rate is present. The methods can also include progressively lowering thresholds for one or more of the cyclic variation in heart rate indices, the tachycardia indices, and the bradycardia indices until one of periodic limb movement sleep disorders, obstructive sleep apneas, or repeated central apneas or Cheyne-Stokes respiration is indicated.

Analyzing the heart rate series can include autocorrelating the heart rate series. Detecting the cyclic variation in heart rate can include scoring autocorrelation measures to characterize a likelihood that the autocorrelation measures indicate a sleep disorder. The measures can include a number of zero crossings of an autocorrelated heart rate series, distances between adjacent zero crossings, and a standard deviation of the distances between adjacent zero crossings. The measures can also include a measure f as given herein. Detecting the cyclic variation in heart rate can include scoring measures of the heart rate series to characterize the likelihood that the heart rate series measures are indicative of a sleep disorder.

Information characterizing aspects of the physiological condition of the monitored individual other than the heart can be reported, as can information characterizing movement of a part of the body other than the heart. An obstructive sleep apnea event can be reported based exclusively on the detection of the cyclic variation in heart rate in the heart rate series.

Other embodiments of this aspect include corresponding systems, apparatus, and computer program products.

Another aspect of the subject matter described in this specification can be embodied in systems that include an electrocardiograph configured to generate an electrocardiogram of a monitored individual, a data processing device configured to detect a sleep disorder of the monitored individual based exclusively on the electrocardiogram, and a transmitter configured to report information characterizing the physiological condition of the monitored individual during the detected sleep disorder.

This and other aspects can include one or more of the following features. The data processing device can be configured to detect the sleep disorder by analyzing a heart rate series derived from the electrocardiogram in the time domain. The data processing device can include an autocorrelator configured to cross correlate the heart rate series with itself and/or a scoring unit to score measures of the autocorrelation of the heart rate series to characterize the likelihood that the autocorrelation measures are indicative of the sleep disorder. The autocorrelation measures can include a number of zero crossings of an autocorrelated heart rate series, distances between adjacent zero crossings, and a standard deviation of the distances between adjacent zero crossings. The autocorrelation measures can also include a measure f as given in this specification.

The scoring unit can also score measures of the heart rate series to characterize the likelihood that the heart rate series measures are indicative of obstructive sleep apnea. The system can also include one or more additional monitoring devices configured to generate information characterizing aspects of the physiological condition of a monitored individual other than activity of the heart. The transmitter can be configured to report the information generated by the additional monitoring devices. The system can also include a beat detector. The electrocardiograph can be a patient portable sensing unit. Other embodiments of this aspect include corresponding methods, apparatus, and computer program products.

The details of one or more implementations are set forth in the accompanying drawings and the description below. Other features and advantages will be apparent from the description and drawings, and from the claims.

DESCRIPTION OF DRAWINGS

FIG. 4 is a collection of scoring activities expressed in pseudo-code.

FIG. 11 is a graph that illustrates heart rate as a function of time in an individual suffering from periodic limb movement disorder.

FIG. 12 is a graph that illustrates heart rate as a function of time in an individual suffering from obstructive sleep apnea.

FIG. 13 is a graph that illustrates heart rate as a function of time in an individual suffering from Cheyne-Stokes respiration.

Like reference symbols in the various drawings indicate like elements.

DETAILED DESCRIPTION

Figure 1:
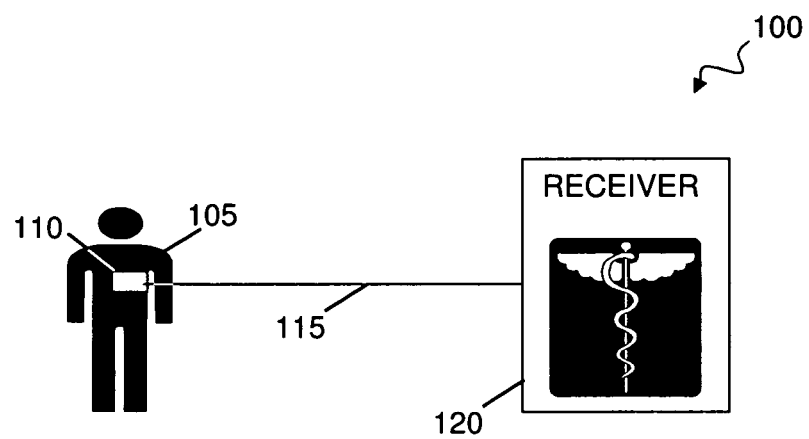
FIG. 1 is a schematic representation of a system in which heart activity is used to detect the existence of sleep disorders in an individual.

FIG. 1 is a schematic representation of a system 100 in which heart activity is used to detect the existence of sleep disorders in an individual. System 100 includes an individual 105, electrocardiograph 110, a data communication path 115, and a receiver 120. Individual 105 can be a patient or a healthy individual who is monitored to detect sleep apnea. Electrocardiograph 110 can include one or more sensing, calibration, filtering, signal processing, control, data storage, and transmission elements suitable for generating and processing an electrocardiogram, as well as relaying a signal characterizing the electrocardiogram over path 115. Electrocardiograph 110 can include an internal communications module for communicating with receiver 120 or exchange data with an external communications module. As discussed further below, electrocardiograph 110 can also include instrumentation for the detection of sleep disorders using an electrocardiogram.

Path 115 can be any suitable medium for data transmission, including wired and wireless media suitable for carrying optical and/or electrical signals. Receiver 120 can include a receiver element for receiving the transmitted signal, as well as various data processing and storage elements for extracting and storing the information carried by the transmission. Receiver 120 can be a medical system in that receiver 120 presents information to medical personnel or to a medical expert system for analysis. Receiver 120 either can reside remotely from instrumentation 110 in that receiver 120 is not located at the same site (e.g., at the same hospital, nursing home, or other medical care facility) as instrumentation 110 or the receiver 120 can reside within the same general area or vicinity as instrumentation 110 (e.g., within the same room, building, or health care facility).

As discussed below, the detection of a sleep disorder using electrocardiogram can influence the transmission of a signal over path 115. For example, the detection of sleep apnea using an electrocardiogram can be used as a trigger for the transmission of a signal that includes information characterizing the physiology of individual 105. Further, the content of the signal can be selected based on the detection of a sleep disorder. By way of example, the transmitted signal can include an indication that sleep apnea has been detected, as well as a excerpts from the electrocardiogram that are indicative of sleep apnea.

Figure 2A:
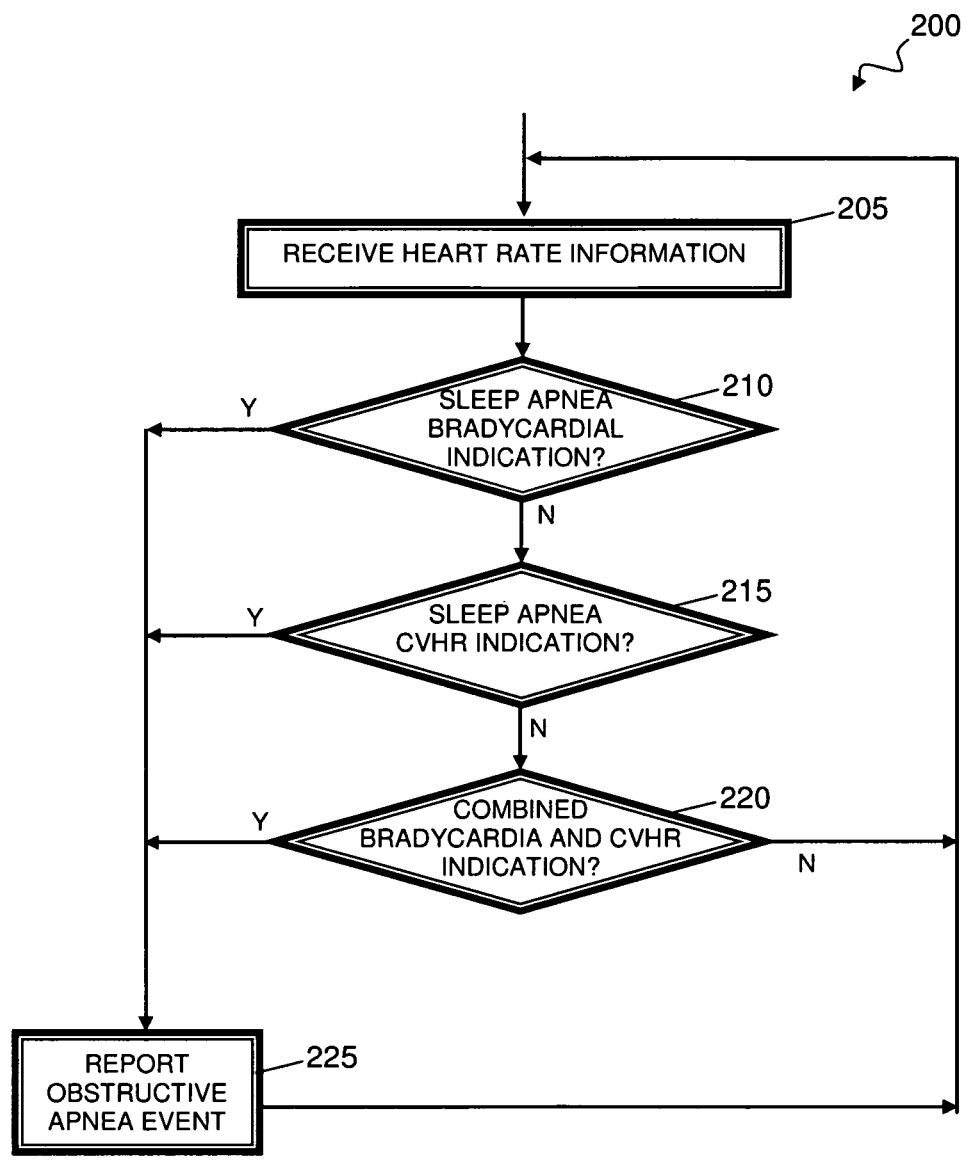
FIGS. 2A and 2B are flow charts of processes for detecting sleep disorders.

FIG. 2A is a flow chart of a process 200 for detecting one class of sleep disorder, namely, obstructive sleep apnea. Process 200 can be performed by one or more digital data processing devices that perform operations by executing one or more sets of machine-readable instructions. For example, process 200 can be performed by a digital data processing device in electrocardiograph 110 in system 100 (FIG. 1).

The system performing process 200 can receive heart rate information (step 205). The heart rate information can characterize the heart rate of an individual over a time interval. For example, the heart rate information can be a heart rate series that is derived from an electrocardiogram using a beat detector.

The system performing process 200 can determine whether obstructive sleep apnea is indicated by bradycardia in the received heart rate information (step 210). In general, bradycardia is a slowness of the heartbeat. In many contexts, bradycardia is said to occur when the heart rate is less than 60 beats per minute for a certain time interval. However, bradycardia can be said to occur at different heart rates in different contexts.

For example, in the context of detecting obstructive sleep apnea, bradycardia can be said to occur when the heart rate of an adult falls below a different threshold, e.g., such as when heart rate falls below a threshold value of 40 beats per minute for a specific time interval. For example, the time interval can have a duration of at least five seconds. If the number of such bradycardial intervals within a second, larger, interval (e.g., 10 minutes) exceeds a threshold, then sleep apnea can be taken as indicated by bradycardia.

In some implementations, the threshold for detecting obstructive sleep apnea can be based on a physiological condition of the monitored individual. For example, a baseline heart rate, or another threshold with a relationship to the baseline heart rate, can be used as the threshold for detecting obstructive sleep apnea. Baseline heart rate is the heart rate of an individual over a baseline interval. In some implementations, the baseline interval is an interval that is much longer than the interval over which bradycardia is detected. Thus, the baseline heart rate can characterize the average heart rate of the individual over a relatively long period of time.

In other implementations, the baseline interval can be identified based on the physiological characteristics of the monitored individual. For example, the baseline interval can be identified as a period in time in which the standard deviation in heart rate is less than a standard deviation threshold. For example, the baseline interval can be an interval of at least 10 seconds in which the standard deviation in heart rate is less than a standard deviation threshold of 2 beats per minute. The baseline interval can be updated, e.g., periodically, for calculation windows of 10 minutes.

In some implementations, the mean and standard deviation of the time between such bradycardial intervals can also be determined, and a score can be assigned to time intervals in which the bradycardial intervals occur based on these measures. In some implementations, these scores can be smoothed to reduce the variability between scores for consecutive and/or proximate time intervals. If the smoothed score exceeds a threshold, then obstructive sleep apnea can be taken as indicated by bradycardia.

The system performing process 200 can also determine whether obstructive sleep apnea is indicated by any cyclic variation in heart rate (CVHR) in the received heart rate information (step 215). CVHR are cycles of increasing and decreasing heart rate and are observed primarily during sleep. In some implementations, the determination of whether obstructive sleep apnea is indicated by CVHR can be based on time domain analysis of a heart rate series. For example, a heart rate series can be cross-correlated, e.g., with itself (i.e., autocorrelated) in order to determine whether observed CVHR indicates obstructive sleep apnea, as discussed further below.

The system performing process 200 can also determine whether obstructive sleep apnea is indicated by a combined consideration of bradycardia and any cyclic variation in heart rate in the received heart rate information (step 220). In particular, even if bradycardia and CVHR are not independently indicative of obstructive sleep apnea (as determined in steps 210, 215), the combination of bradycardia and CVHR may still be indicative of obstructive sleep apnea. An analysis that combines consideration of bradycardia and CVHR can thus relax the standards applied independently to bradycardia and CVHR in steps 210, 214. As discussed further below, the combination of bradycardia and cyclic variation in heart rate can be taken as indicative of obstructive sleep apnea by comparing indices of bradycardia and cyclic variation in heart rate with indices of tachycardia during the same interval.

If the system performing process 200 determines that obstructive sleep apnea is not indicated by any of bradycardia, cyclic variation in heart rate, or a combined consideration of bradycardia and any cyclic variation in heart rate, then the system can return to receive more heart rate information at step 205.

If the system performing process 200 determines that obstructive sleep apnea is indicated by bradycardia, by any cyclic variation in heart rate, or by a combined consideration of bradycardia and any cyclic variation in heart rate, the system can report an obstructive apnea event at 225. An event is a time interval when the information content of a signal is deemed to be of increased relevance to a particular purpose for which the signal is monitored. In the present context, an obstructive sleep apnea event is a time interval when the information content of the received heart rate information is indicative of obstructive sleep apnea. A obstructive sleep apnea event (or other event) can be reported, e.g., by transmitting an indication of that sleep apnea has occurred, along with information characterizing aspects of the physiological condition of a monitored individual during the event, to a receiver such as receiver 120 (FIG. 1).

Figure 2B:
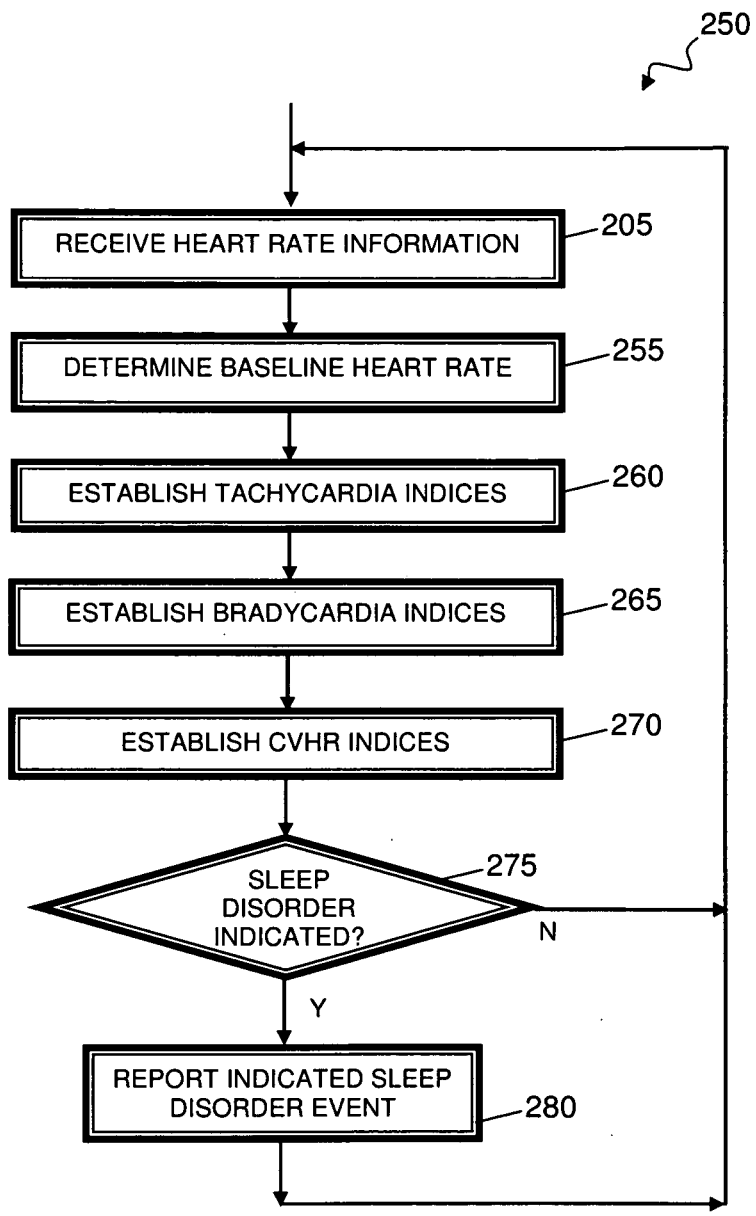

FIG. 2B is a flow chart of a process 250 for detecting and distinguishing between different classes of sleep disorders. Process 250 can be performed by one or more digital data processing devices that perform operations by executing one or more sets of machine-readable instructions. For example, process 250 can be performed by a digital data processing device in electrocardiograph 110 in system 100 (FIG. 1). Process 250 can be performed in isolation or in conjunction with other activities. For example, all or a portion of process 200 (FIG. 2A) can be performed determine whether there is a sleep disorder indication at 270, as discussed further below.

The system performing process 200 can receive heart rate information (step 205) and determine a baseline heart rate from the received heart rate information (step 255). As discussed above, baseline heart rate is the heart rate of an individual over a baseline interval. In some implementations, the baseline interval is an interval that is much longer than the interval over which bradycardia is detected. Thus, the baseline heart rate can characterize the average heart rate of the individual over a relatively long period of time.

In other implementations, the baseline interval can be identified based on the physiological characteristics of the monitored individual. For example, the baseline interval can be identified as a period in time in which the standard deviation in heart rate is less than a standard deviation threshold. For example, the baseline interval can be an interval of at least 10 seconds in which the standard deviation in heart rate is less than a standard deviation threshold of 2 beats per minute. The baseline interval can be updated, e.g., periodically, for calculation windows of 10 minutes.

The system performing process 250 can establish whether one or more indices of tachycardia are present in the received heart rate information (step 260). In general, tachycardia is a rapid heartbeat. In many contexts, tachycardia is said to occur when the heart rate is greater than 100 beats per minute for a certain time interval. Tachycardia indices are derived from the received heart rate information and indicate that an individual has tachycardia.

However, tachycardia can be indicated at different heart rates in different contexts. For example, in the context of detecting sleep disorders, tachycardia can be indicated by the heart rate of a monitored individual rising above a threshold that is based on a physiological condition of the monitored individual. Example of thresholds that are based on a physiological condition of the monitored individual include the baseline heart rate or another threshold with a relationship to the baseline heart rate. In some implementations, tachycardia indices can be defined as an increase above a baseline heart rate for an interval that is longer than a specified interval. For example, heart rate of 10 bpm or more above the baseline heart rate for intervals that are longer than five seconds can be established as indices of tachycardia.

In some implementations, the number of such increases above a baseline heart rate within a longer interval (e.g., an interval of 10 minutes), as well as the statistical measures of such increases, can themselves be established as indices of tachycardia. For example, the mean number of such increases above a baseline heart rate, and the standard deviation in the timing of such increases, can be established as indices of tachycardia.

The system performing process 250 can establish whether one or more indices of bradycardia are present in the received heart rate information (step 265). For example, in some implementations, bradycardia indices can be defined as an decrease below a baseline heart rate for an interval that is longer than a specified interval. For example, heart rate of 10 bpm or more below the baseline heart rate for intervals that are longer than five seconds can be established as indices of bradycardia.

In some implementations, the number of such decreases below a baseline heart rate within a longer interval (e.g., an interval of 10 minutes), as well as the statistical measures of such decreases, can themselves be established as indices of bradycardia. For example, the mean number of such decreases below a baseline heart rate, and the standard deviation in the timing of such decreases, can be established as indices of bradycardia.

The system performing process 250 can establish whether one or more indices of cyclic variation in heart rate are present in the received heart rate information (step 270). In some implementations, the establishment of indices of cyclic variation in heart rate can be based on time domain analysis of a heart rate series. For example, a heart rate series can be cross-correlated, e.g., with itself (i.e., autocorrelated) in order to establish whether cyclic variation in heart rate is indicated, as discussed further below.

The system performing process 250 can also determine whether a sleep disorder is indicated, as well as the class of any indicated sleep disorder, using any tachycardia indices, bradycardia indices, and cyclic variation in heart rate indices that have been established during a time interval (step 275).

In general, the determination of whether a sleep disorder is indicated can be based on a scoring of the indices. The indices can be scored both individually and collectively. For example, tachycardia indices can be scored individually to determine whether tachycardia is present, bradycardia indices can be scored individually to determine whether bradycardia is present, and cyclic variation in heart rate indices can be scored individually to determine whether cyclic variation in heart rate is present. As yet another example, tachycardia indices, bradycardia indices, and variation in heart rate indices can be scored collectively to determine whether they collectively indicate that a sleep disorder is present.

Based on the scores yielded by such scoring, a determination of whether a sleep disorder is indicated, as well as the class of any indicated sleep disorder, can be made. For example, if:

individual scoring of tachycardia indices indicates that tachycardia is present;

individual scoring of cyclic variation in heart rate indices indicates that cyclic variation in heart rate is present; and individual scoring of bradycardia indices indicates that bradycardia is not present, then periodic limb movement sleep disorders are indicated.

FIG. 11 is a graph 1100 that illustrates heart rate as a function of time in an individual suffering from periodic limb movement disorder. As shown, heart rate cyclically increases above a threshold baseline heart rate 1105 during an interval 1110 in which both tachycardia and cyclic variation in heart rate are present. Further, bradycardia is not present during interval 1110.

As another example, if:

individual scoring of bradycardia indices indicates that bradycardia is present;

individual scoring of cyclic variation in heart rate indices d indicates that cyclic variation in heart rate is present; and individual scoring of tachycardia indices indicates that tachycardia is not present, then obstructive sleep apneas are indicated.

FIG. 12 is a graph 1200 that illustrates heart rate as a function of time in an individual suffering from obstructive sleep apnea. As shown, heart rate cyclically falls below a threshold baseline heart rate 1205 during an interval 1210 in which both bradycardia and cyclic variation in heart rate are present. Further, tachycardia is not present during interval 1210.

As yet another example, if:

individual scoring of bradycardia indices indicates that bradycardia is present;

individual scoring of cyclic variation in heart rate indices indicates that cyclic variation in heart rate is present;

individual scoring of tachycardia indices indicates that tachycardia is present; and collective scoring of tachycardia indices, bradycardia indices, and variation in heart rate indicates that a sleep disorder is present;

then repeated central apneas or Cheyne-Stokes respiration are indicated.

FIG. 13 is a graph 1300 that illustrates heart rate as a function of time in an individual suffering from Cheyne-Stokes respiration. As shown, heart rate cyclically falls below and rises above a threshold baseline heart rate 1305 during an interval 1310 in which tachycardia, bradycardia, and cyclic variation in heart rate are all present.

As yet another example, if:

individual scoring of bradycardia indices indicates that bradycardia is not present;

individual scoring of cyclic variation in heart rate indices indicates that cyclic variation in heart rate is present; and individual scoring of tachycardia indices indicates that tachycardia is not present, then repeated central apneas or Cheyne-Stokes respiration are indicated.

Graph 1300 also illustrates that tachycardia and bradycardia need not always be present in an individual suffering from Cheyne-Stokes respiration. For example, during interval 1315, the magnitude of the cyclical changes in heart rate are too small to be taken as indicative of tachycardia and bradycardia. Nevertheless, the cyclic variation in heart rate during interval 1315 indicates that the individual is suffering from Cheyne-Stokes respiration.

As yet another example, if:

individual scoring of bradycardia indices determines that bradycardia is not present;

individual scoring of cyclic variation in heart rate indices indicates that cyclic variation in heart rate is not present;

individual scoring of tachycardia indices indicates that tachycardia is not present, and collective scoring of tachycardia indices, bradycardia indices, and variation in heart rate indices indicates that a sleep disorder is present;

then the thresholds for the individual scores will be progressively lowered until one of periodic limb movement sleep disorders, obstructive sleep apneas, or repeated central apneas or Cheyne-Stokes respiration is indicated.

Returning to FIG. 2B, if the system performing process 250 determines that a sleep disorder is indicated, the system can report the indicated sleep disorder event at 280. The report can include information identifying the class of any indicated sleep disorder. The sleep disorder can be reported, e.g., by transmitting an indication of that sleep disorder has occurred, along with information characterizing aspects of the physiological condition of a monitored individual during the event, to a receiver such as receiver 120 (FIG. 1).

Figure 3:
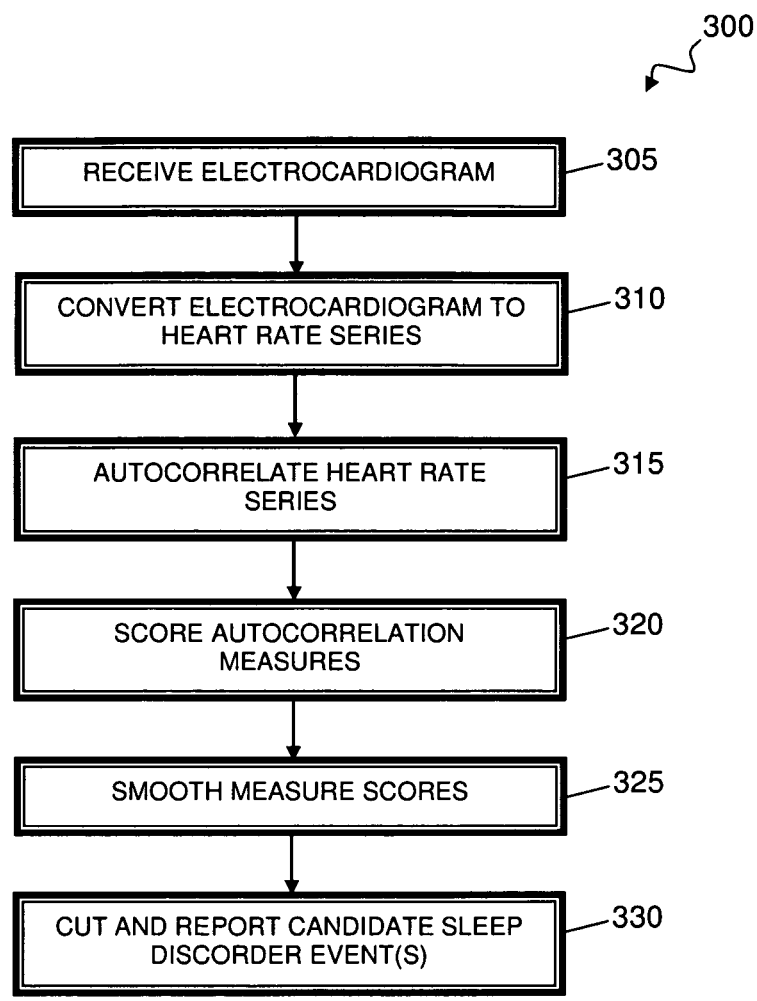
FIG. 3 is a flow chart of a process for detecting sleep disorders.

FIG. 3 is a flow chart of a process 300 for identifying sleep disorders using cyclic variation in heart rate. Process 300 can be performed by one or more digital data processing devices that perform operations by executing one or more sets of machine-readable instructions. For example, process 300 can be performed by a digital data processing device in electrocardiograph 110 in system 100 (FIG. 1). Process 300 can be performed in isolation or in conjunction with other activities. For example, all or a portion of process 300 can be performed as part of various steps in process 200 (FIG. 2A). As another example, all or a portion of process 300 can be performed as part of various steps in process 250 (FIG. 2B).

The system performing process 300 can receive an electrocardiogram (step 305) and convert the received electrocardiogram into a heart rate series (step 310). For example, the electrocardiogram can be converted into a heart rate series by a beat detector included in electrocardiograph 110 in system 100 (FIG. 1).

In some implementations, the electrocardiogram can be screened to ensure that the electrocardiogram does not include other cardiac rhythm conditions. For example, the electrocardiogram can be screened to ensure that the monitored individual is not currently undergoing atrial fibrillation, atrial flutter, ventricular fibrillation, ventricular flutter, or supraventricular tachycardia. If the monitored individual is subject to such a cardiac rhythm condition, then the system can exclude a portion of the electrocardiogram from further analysis. For example, the system can exclude 10 minutes or so of an electrocardiogram from further analysis upon detection of another cardiac rhythm condition.

In some implementations, the electrocardiogram can also be screened to ensure that the electrocardiogram does not include excessive noise that hinders accurate detection of sleep disorders. Such noise can arise, e.g., due to movement of the monitored individual and/or the monitoring system during sleep. If the electrocardiogram includes too much noise, then the system can exclude a portion of the electrocardiogram from further analysis. For example, the system can exclude 10 minutes or so of an electrocardiogram from further analysis.

In some implementations, the electrocardiogram can also be screened to ensure that the electrocardiogram does not include an excessive number of ectopic beats. Ectopic beats are heart beats that originate somewhere other than the sinoatrial node. Ectopic beats can be detected by analysis of the electrocardiogram itself. For example, in some implementations, ectopic beats can be characterized by the following conditions being met:

-if $|d_1| < 0.3$ AND  (Equation 1)

(if $d_2 < -0.2$ and $d_3 < 0.4$;

if $d_2 > 0.2$ and $d_3 < -0.4$;

if $d_2 > 0.5$ and $d_3 < -0.5$; OR if $d_2 < -0.4$ and $d_3 > 0.4$), where $$d_1 = \frac{(RR(i-1) - RR(i-2))}{RR(i-2)} \quad \text{Equation 2}$$

$$d_2 = \frac{(RR(i) - RR(i-1))}{RR(i-1)} \quad \text{Equation 3}$$

$$d_3 = \frac{(RR(i+1) - RR(i))}{RR(i)} \quad \text{Equation 4}$$

and RR(i) is the R-to-R interval of beat i, RR(i+1) is the R-to-R interval of the beat following beat i, RR(i−1) is the R-to-R interval of the beat preceding beat i, and RR(i+2) is the R-to-R interval of the beat following beat i+1, then an ectopic beat can be identified.

In other implementations, ectopic beats can be characterized by the following conditions being met:

if $|d_1|<0.5$ AND (if $d_2<-0.2$ and $d_3>0.4$; OR if $d_2>0.2$ and $d_3<-0.4$)  (Equation 5)

where $d_1$, $d_2$, and $d_3$ are as defined in Equations 2, 3, and 4, then an ectopic beat can be identified.

In some implementations, an excessive number of ectopic beats is more than 50% of the beats within a time interval (e.g., within one minute). If the electrocardiogram includes too many ectopic beats, then the system can exclude a portion of the electrocardiogram from further analysis. For example, the system can exclude 10 minutes or so of an electrocardiogram from further analysis.

The system performing process 300 can autocorrelate the heart rate series (step 315). Autocorrelation of the heart rate series cross-correlates the heart rate series with itself identify frequency patterns. Once example of a frequency pattern that can be identified is CVHR. Autocorrelation of the heart rate series can yield measures and indices of CVHR, and the system performing process 300 can score those measures and indices to characterize the likelihood that the measures are indicative of sleep apnea (step 320). In some implementations, the measures and indices yielded by autocorrelation of a heart rate series include the number of zero crossings of the autocorrelated heart rate series (hereinafter "num"), the distances between these adjacent zero crossings, the standard deviation of these distances (hereinafter "sd"); and a measure "f" given by:

$$f = \frac{1000}{L*mRR} \quad \text{Equation 6}$$

where "L" is the mean distance between these adjacent zero crossings over a time interval and "mRR" is the mean (i.e., the average) RR interval over a time interval. Generally, L and mRR are taken over the same time interval, e.g., the same minute.

The system performing process 300 can score the autocorrelation measures and indices based on how likely the autocorrelation measures are indicative of sleep disorders (step 320). The scoring can be done for time intervals that span several heart beats. For example, the autocorrelation measures can be scored on a minute-by-minute basis.

In some implementations, the scoring can also be based on measures that are derived directly from the heart rate series. In such measures, peaks (local maximum points) and troughs (local minimums) can be identified directly from heart rate series. For example, the scoring can also be based on one or more of the following parameters: the mean heart rate (hereinafter "mHR"); the standard deviation of heart rate ("sdHR"); the number of peaks in heart rate("PkNum"); the mean amplitude of the peak-to-trough variation in heart rate in beats per minute ("mAmp"); the standard deviation of this mean amplitude ("sdAmp"); the mean distance between peaks in heart rate ("mPkDist"); and the standard deviation of distance between peaks ("sdPkDist"). In some implementations, the combined autocorrelation measures and heart rate series measures and indices are scored in accordance with the scoring activities 400 shown in pseudo-code in FIG. 4. Scoring activities 400 can be implemented using, e.g., a software module or other scoring unit. Such a scoring unit can be located at a digital data processing device in electrocardiograph 110 in system 100 (FIG. 1).

Returning to FIG. 3, the system performing process 300 can smooth the measure scores (step 325). Smoothing the measure scores can reduce the variability between scores for consecutive and/or proximate time intervals. For example, the measure scores can be smoothed by averaging a number of scores for a number of consecutive and/or proximate time intervals. Such consecutive and/or proximate time intervals can be said to form a "detection interval." In some implementations, the measure scores are smoothed by averaging ten scores of 10 consecutive minute-long intervals. Hence, the detection interval is these implementations is 10 minutes long.

The system performing process 300 can cut and report one or more candidate sleep disorder events (step 330). Candidate sleep disorder events can be detected based on the smoothed measure scores exceeding a threshold indicative of a sleep disorder event. For example, in the context of measure scoring activities 400 (FIG. 4) and a smoothing by averaging the measure scores of 10 consecutive minutes, a score in excess of 60 with a detection interval of 10 minutes and a maximum exceeding 80 within this interval can be taken as a candidate sleep disorder event.

"Cutting" an event generally includes separating information descriptive of aspects of the physiological condition of a monitored individual over a first interval from a larger collection of information descriptive of aspects of the physiological condition of the monitored individual over a second interval, where the first interval is generally much shorter than the second interval. For example, an electrocardiogram that characterizes the electrical activity of the heart during a sleep disorder event can be cut from an electrocardiogram that characterizes the electrical activity of the heart over a longer period of time, e.g., over the entire night.

Figure 5:
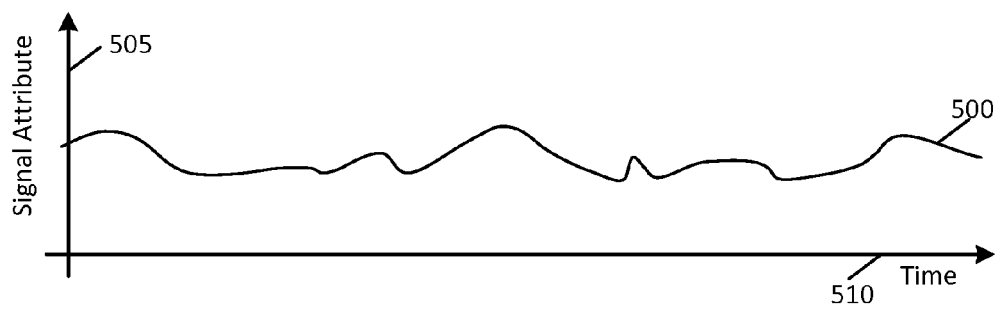
FIGS. 5 and 6 schematically illustrate the relationship between events and a monitoring interval.
Figure 6:
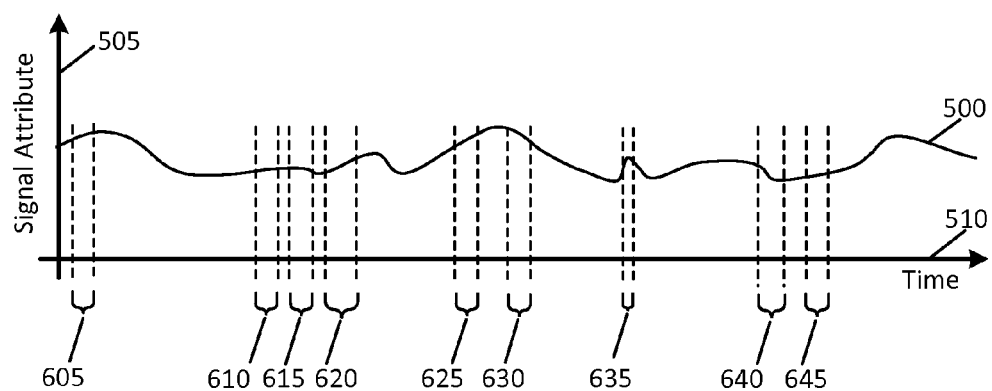

FIGS. 5 and 6 schematically illustrate the relationship between events and a monitoring interval. In particular, FIG. 5 shows an example of a biological signal 500. Biological signal 500 characterizes a physiological condition of a monitored individual over a monitoring interval. For example, biological signal 500 can be an electrocardiogram or a heart rate series. Biological signal 500 is time variant in that an attribute 505 of biological signal 500 changes with time 510. Attribute 505 of biological signal 500 may continuously change with time and may never reach a steady state value as activity level, metabolic rate, or other factors vary over the course of days, weeks, or even longer intervals of time.

Although attribute 505 of biological signal 500 may change continuously over the monitoring interval, all of the changes may not have the same relevance to a particular purpose for which the biological signal 500 is monitored. FIG. 6 shows the biological signal 500 having a series of events 605, 610, 615, 620, 625, 630, 635, 640, 645 identified. Events 605, 610, 615, 620, 625, 630, 635, 640, 645 are time intervals when the information content of biological signal 500 is deemed to be of increased relevance to a particular purpose for which biological signal 500 is monitored. For example, in the context of system 100 (FIG. 1), events 605, 610, 615, 620, 625, 630, 635, 640, 645 are time intervals when the information content of biological signal 500 is deemed to be indicative of a sleep disorder.

Events 605, 610, 615, 620, 625, 630, 635, 640, 645 need not be of equal or predetermined duration. For example, event 635 is shorter than event 620. Moreover, events 605, 610, 615, 620, 625, 630, 635, 640, 645 need not be limited based on the activities performed to determine that events 605, 610, 615, 620, 625, 630, 635, 640, 645 include information of increased relevance. For example, in the context of process 400 (FIG. 4), candidate sleep disorder events can be detected based on the average of measure scores over a detection interval (e.g., of 10 minutes) exceeding a threshold indicative of a sleep disorder. However, the events which are cut and reported need not be of the same duration as this detection interval. For example, in the context of measure scoring activities 400 (FIG. 4), a sleep disorder event can encompass the time during which the average measure scores of 10 consecutive minutes exceeded 20, provided that the mean heart rate ("mHR") during this period is in excess of 40 bpm. Thus, in general, a sleep disorder event can begin before the detection interval and can end after the detection interval.

Figure 7:
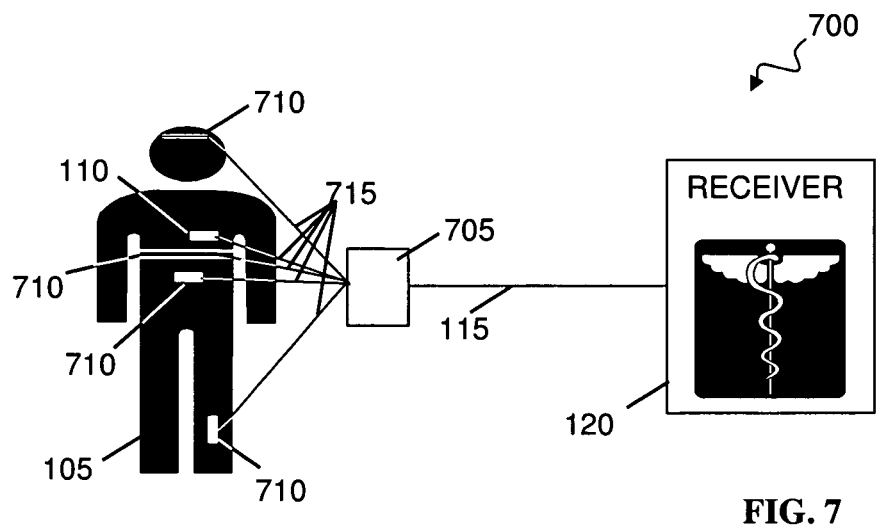
FIG. 7 is a schematic representation of a system in which heart activity is used to detect sleep disorders.

FIG. 7 is a schematic representation of a system 700 in which heart activity is used to detect sleep disorders. In addition to individual 105, electrocardiograph 110, data communication path 115, and receiver 120, system 700 includes a communications module 705 and one or more additional monitoring devices 710.

Communications module 705 is a device that manages the exchange of information between electrocardiograph 110 and one or more monitoring devices 710 and receiver 120. Communications module 705 can be external to electrocardiograph 110 and monitoring devices 710 and exchange information with electrocardiograph 110 and monitoring devices 710 over two or more wired or wireless data communication paths 715. Communications module 705 can thus include transceivers for data communication with electrocardiograph 110, monitoring devices 710, and receiver 120. In some implementations, communications module 705 can be divided into a sensor module and a monitor module, as discussed further below.

Monitoring devices 710 are devices for generating signals that include information characterizing aspects of the physiological condition of individual 105. Example monitoring devices 710 include an electroencephalographs, electrooculographs, electromyographs, blood oxygen sensors (including pulse oximeters), airflow transducers, movement sensors, and the like. Monitoring devices 710 can thus characterize aspects of the physiological condition of individual 105 other than the heart.

In operation, sleep disorders can be detected using an electrocardiography signal generated by electrocardiograph 110. In some implementations, sleep disorders can be detected based exclusively on such an electrocardiography signal, i.e., without reliance on other biological signals generated by monitoring devices 710. Such detection is particularly appropriate in situations where all of the monitoring devices used in traditional polysomnography are not present, or when the biological signals generated by such monitoring devices are too noisy or otherwise inappropriate for use.

Figure 8:
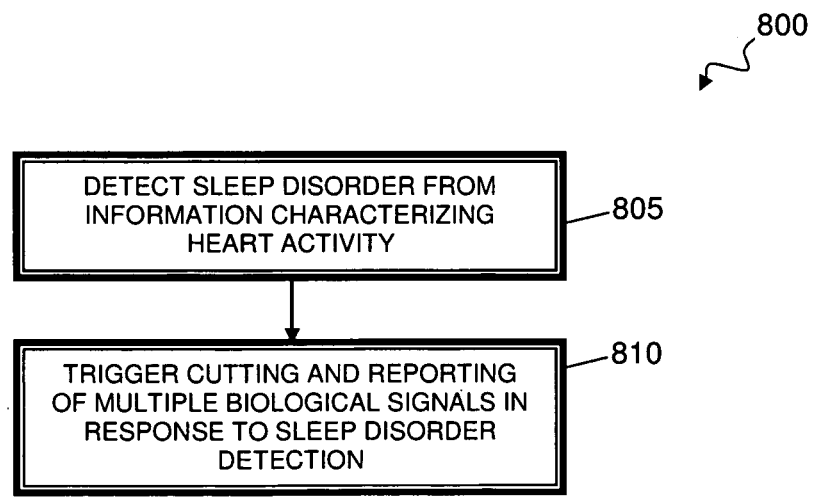
FIG. 8 is a flow chart of a process for detecting sleep disorders.

FIG. 8 is a flow chart of a process 800 for detecting sleep disorders. Process 800 can be performed by one or more digital data processing devices that perform operations by executing one or more sets of machine-readable instructions. For example, process 800 can be performed by a digital data processing device in electrocardiograph 110, in communications module 705, or elsewhere in system 700 (FIG. 7). Process 800 can be performed in isolation or in conjunction with other activities. For example, all or a portion of process 800 can be performed in conjunction with process 200 (FIG. 2A), process 250 (FIG. 2B), process 300 (FIG. 3), or combinations of two or more of these processes.

The system performing process 800 can detect sleep disorder from information characterizing heart activity (step 805). For example, in some implementations, obstructive sleep apnea can be detected by determining whether heart rate information includes a bradycardial indication of sleep apnea, a CVHR indication of obstructive sleep apnea, or both. An example of such a detection is described in process 200 (FIG. 2A). As another example, in some implementations, a sleep disorder can be detected using time domain analysis of a electrocardiograph. An example of such a detection is described in process 300 (FIG. 3).

The system performing process 800 can trigger cutting and reporting of multiple biological signals based on the detection of a sleep disorder (step 810). The multiple biological signals can be generated by multiple monitoring devices, such as monitoring devices 710 (FIG. 7). As a result, a sleep disorder event can be characterized in a report by information characterizing heart activity, as well as information characterizing other aspects of the physiological condition of a monitored individual. For example, a sleep disorder event can be characterized in a report by information characterizing the electrical activity of the brain, the electrical activity associated with eye movements, the electrical activity associated with other muscular activity or movements, blood oxygen saturation, and movement of various parts of the body.

Such a cutting of multiple biological signals allows various aspects of the physiology of a monitored individual to be characterized in a report without undue burden on communication systems. In particular, since the duration of a event is generally much shorter than the interval in which the event occurs, the amount of transmitted data can be reduced.

Figure 9:
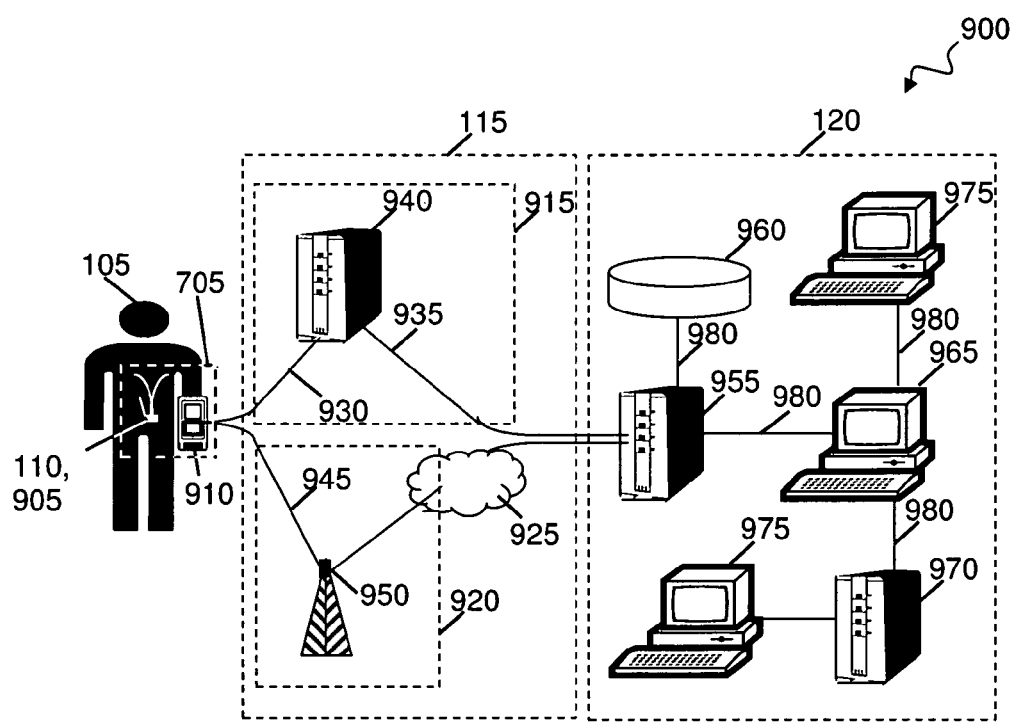
FIG. 9 is a schematic representation of a system in which heart activity is used to detect sleep disorders.

FIG. 9 is a schematic representation of a system 900 in which heart activity is used to detect sleep disorders. System 900 includes individual 105, electrocardiograph 110, signal path 115, receiver 120, and communications module 705. Communications module 705 is divided into a sensor module 905 and a monitor module 910. Sensor module 905 includes electrocardiograph 110 (e.g., three ECG leads with electrodes), as well as a two channel ECG signal recorder and a wireless and/or wired data output. Sensor module 905 can also include a clip for attaching sensor module to a belt, a neckpiece, or other item worn by individual 105. Sensor module 905 can thus be facilely portable by individual 105.

Monitor module 910 includes a data input that is adapted to receive data output from sensor module 905 as well as one or more wireless and/or wired data outputs for data communication over signal path 115. In some implementations, monitor module 910 can also include one or more additional data inputs that are adapted to receive information from additional monitoring devices, such as monitoring devices 710 (FIG. 7) (not shown).

Monitor module 910 includes one or more digital data processing devices that perform operations by executing one or more sets of machine-readable instructions. The operations performed at monitor module 910 can include the activities of one or more of process 200 (FIG. 2), process 300 (FIG. 3), and process 800 (FIG. 8). In some implementations, monitor module 910 can be a desktop instrument. In other implementations, monitor module 910 can be a portable device such a personal digital assistant (PDA).

Signal path 115 can include one or both of a wired data link 915 and a wireless data link 920 coupled to a data network 925 to place instrumentation 110 in data communication with receiver 120. Wired data link 915 includes a public network portion 930 and a private or virtual private network portion 935 bridged by a server 940. Public network portion 930 provides for data communication between instrumentation 110 and server 940 over a wired data link such as a telephone network. Private network portion 935 provides for private or virtually private data communication from server 940 to receiver 120. Server 940 can interface for data communication with both portions 930, 935. For example, server 940 can communicate directly with receiver 120 using the peer-to-peer protocol (PPP).

Wireless data link 945 can include one or more wireless receivers and transmitters 950 such as a WiFi receiver, a cellular phone relay station, and/or other cellular telephone infrastructure to place instrumentation 110 in data communication with data network 925. In turn, data network 925 communicates with receiver 120.

Receiver 120 includes a receiver server 955, a data storage device 960, a call router 965, a communications server 970, and one or more application servers 975 that are all in data communication with one another over one or more data links 980. Receiver server 955 is a data processing device that receives and transmits communications over signal path 115 and relays incoming communications to data storage device 960 and call router 965 in accordance with the logic of a set of machine-readable instructions. Data storage device 960 is a device adaptable for the storage of information. Data storage device 960 can be a volatile and/or non-volatile memory that records information electrically, mechanically, magnetically, and/or optically (such as a disk drive). Call router 965 is a data processing device that, in accordance with the logic of a set of machine-readable instructions, identifies the content of an incoming communication and directs the communication to one or more appropriate application servers 975 based on that content. Communications server 970 is a data processing device that relays communications between call router 965 and one or more application servers 975 over an external network. Application servers 975 are data processing devices that interact with a user or operate in isolation to provide one or more monitoring services in accordance with the logic of a set of machine-readable instructions. Data links 980 can be part of a local area and/or private network or part of a wide area and/or public network.

In operation, electrocardiograph 110 of sensor module 905 can sense, amplify, and record electrical signals relating to the activity of the heart. Sensor module 905 can relay all or a portion of those signals to monitor module 910 where they can be stored or otherwise managed. As part of the management, monitor module 910 can store the signals locally and transmit event excerpts from the signals to receiver 120. The transmitted signals pass along data link 115 over one or more of wired data link 915 and wireless data link 920 to receiver 120. At receiver 120, the signals are received by server 955 which causes at least a portion of the incoming signals to be stored on data storage device 960 and relayed to call router 965.

The incoming signals relayed to call router 965 are directed to one or more appropriate application servers 975 based on the content of the signals. For example, when the signal relates to a certain class of sleep disorder, the signal can be directed to a certain application server 975 that is accessible to a sleep specialist having expertise with that sleep disorder. As another example, when the signal originates with an individual who is under the care of a particular physician, the signal can be directed to a certain application server 975 that is accessible to that physician. When appropriate, a signal can be routed to communications server 970 which in turn relays the signal to the appropriate application server 975 over an external network.

Communications can also be relayed from receiver 120 back to individual 105 or to other individuals. For example, when a physician or expert system identifies that care is needed, a message requesting that the individual seek care can be returned to individual 105 over data link 115. In urgent care situations, third parties such as medical personnel can be directed to individual 105, either by receiver 120 or by instrumentation 110.

Figure 10:
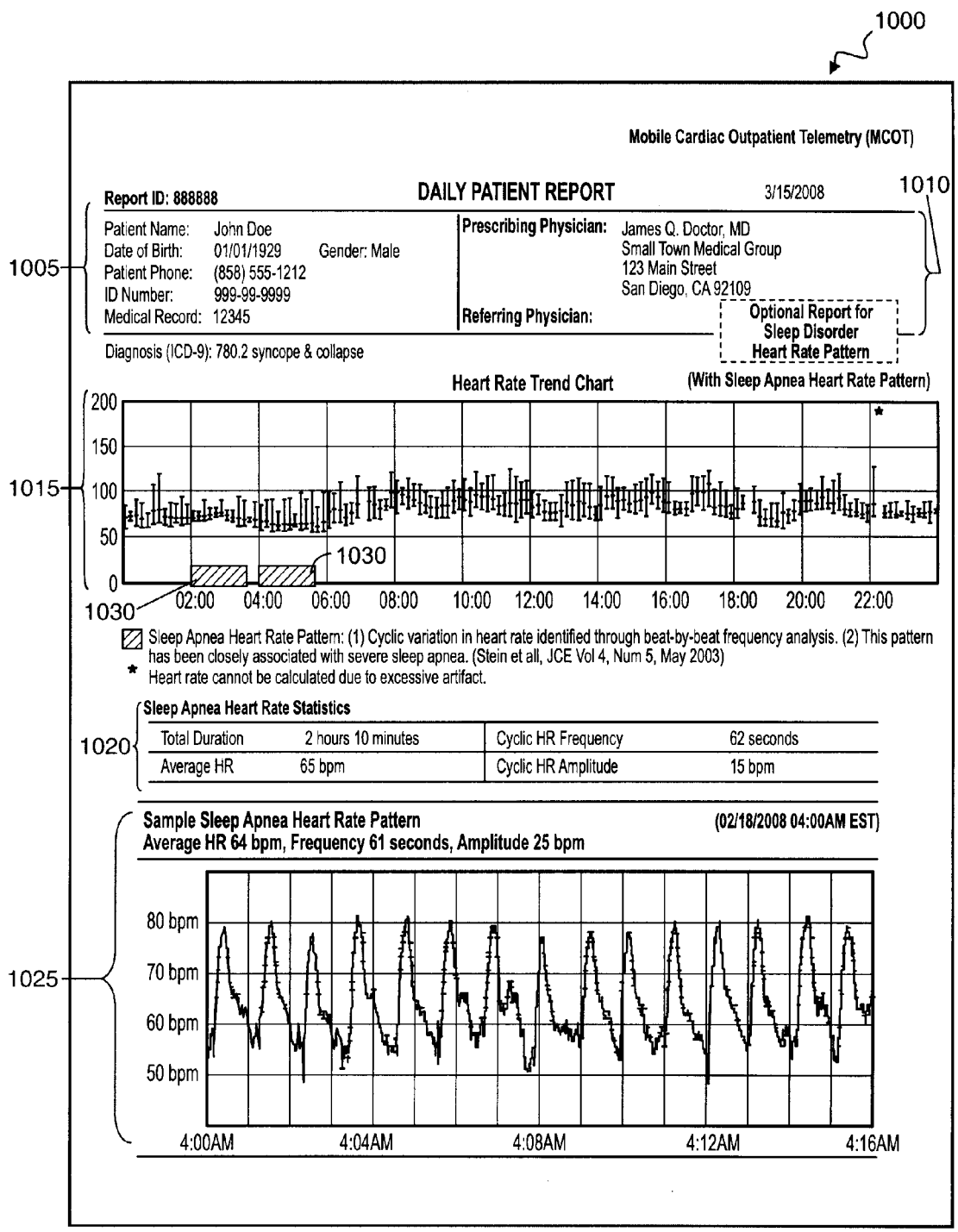
FIG. 10 is a schematic representation of a report in which a sleep disorder event is characterized for medical personnel.

FIG. 10 is a schematic representation of a report 1000 in which a sleep disorder event is characterized for medical personnel. Report 1000 is limited to information that characterizes the activity of the heart. However, as mentioned above, reports that characterize sleep disorder events can also include information characterizing other aspects of the physiological condition of a patient.

Report 1000 includes monitored individual identification information 1005, heart activity reporting area 1015, sleep apnea summary reporting area 1020, and sleep apnea event reporting area 1025. Individual identification information 1005 includes text or other information identifying a monitored individual, such as name, date of birth, age, gender, and the like. Individual identification information 1005 can also includes text or other information 1010 characterizing the medical care received by the monitored individual, such as the names of prescribing and referring physicians.

Heart activity reporting area 1015 includes text or other information characterizing the heart activity of a monitored individual over a reporting interval. For example, heart activity reporting area 1015 can graphically characterize the average heart rate of an individual over an overnight reporting interval, as well as the variability in heart rate during that time, as shown. In some implementations, the reporting interval is the entire time which an individual is monitored, i.e., the entire monitoring interval. In some implementations, the reporting interval is a portion of the monitoring interval.

In some implementations, heart activity reporting area 1015 can also include one or more sleep apnea event identifiers 1030. Sleep apnea event identifiers 1030 are visual indicia that identify intervals in the reporting interval in which sleep apnea is detected.

Sleep apnea summary reporting area 1020 includes text or other information that summarizes sleep apnea detection during the reporting interval. For example, sleep apnea summary reporting area 1020 can characterize the total duration of sleep apnea events in the reporting interval, the average heart rate during the events in the reporting interval, frequency of the cyclic variation in heart rate during the events in the reporting interval, and the amplitude of the cyclic variation in heart rate during the events in the reporting interval.

Sleep apnea event reporting area 1025 includes text or other information that characterizes one or more individual sleep apnea events during the reporting interval. For example, sleep apnea event reporting area 1025 can characterize the duration of an individual sleep apnea event in the reporting interval, the average heart rate during the sleep apnea event, frequency of the cyclic variation in heart rate during the sleep apnea event, and the amplitude of the cyclic variation in heart rate during the sleep apnea event. In some implementations, sleep apnea event reporting area 1025 can also graphically characterize the heart rate of an individual during such an individual event, as shown.

Embodiments of the subject matter and the functional operations described in this specification may be implemented in digital electronic circuitry, or in computer software, firmware, or hardware, including the structures disclosed in this specification and their structural equivalents, or in combinations of one or more of them. Embodiments of the subject matter described in this specification may be implemented as one or more computer program products, i.e., one or more modules of computer program instructions encoded on a tangible data storage device for execution by, or to control the operation of, data processing device.

The term "data processing device" encompasses all apparatus, devices, and machines for processing data, including by way of example a programmable processor, a computer, or multiple processors or computers. The devices may include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) may be written in any form of programming language, including compiled or interpreted languages, or declarative or procedural languages, and it may be deployed in any form, including as a stand alone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform functions by operating on input data and generating output. The processes and logic flows may also be performed by, and apparatus may also be implemented as, special purpose logic circuitry, e.g., an FPGA (field programmable gate array) or an ASIC (application specific integrated circuit).

Processor suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer may be embedded in another device, e.g., a mobile telephone, a personal digital assistant (PDA), a mobile audio or video player, a game console, a Global Positioning System (GPS) receiver, to name just a few.

Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory may be supplemented by, or incorporated in, special purpose logic circuitry.

To provide for interaction with a user, embodiments of the subject matter described in this specification may be implemented on a data processing device having a display device, e.g., a CRT (cathode ray tube) or LCD (liquid crystal display) monitor, for displaying information to the user and a keyboard and a pointing device, e.g., a mouse or a trackball, by which the user may provide input to the computer. Other kinds of devices may be used to provide for interaction with a user as well; for example, feedback provided to the user may be any form of sensory feedback, e.g., visual feedback, auditory feedback, or tactile feedback; and input from the user may be received in any form, including acoustic, speech, or tactile input.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments may also be implemented in combination in a single embodiment. Conversely, various features that are described in the context of a single embodiment may also be implemented in multiple embodiments separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments, and it should be understood that the described program components and systems may generally be integrated together in a single software product or packaged into multiple software products.

Particular embodiments of the subject matter described in this specification have been described. Other embodiments are within the scope of the following claims. For example, the actions recited in the claims may be performed in a different order and still achieve desirable results. As one example, the processes depicted in the accompanying figures do not necessarily require the particular order shown, or sequential order, to achieve desirable results. Accordingly, other implementations are within the scope of the following claims.

What is claimed is:

1. An apparatus comprising one or more machine-readable data storage media storing instructions operable to cause one or more data processing machines to perform operations, the operations comprising:

receiving machine-readable heart rate information characterizing a heart rate of a monitored individual over a detection window;

determining a quantity of bradycardia events present in at least a portion of the received heart rate information, wherein the determining comprises:

deciding that a bradycardia event has occurred when at least one of the following is true: (i) the heart rate of the monitored individual is below a predetermined threshold and (ii) the heart rate of the monitored individual is below a baseline heart rate derived from at least a portion of the received heart rate information;

detecting a cyclic variation in the received heart rate information;

determining that obstructive sleep apnea is indicated over the detection window based on a combined analysis of the quantity of bradycardia events present in the received heart rate information and the detected cyclic variation in the received heart rate information; and selectively and individually reporting the obstructive sleep apnea event in real time in response to the determination that sleep apnea is indicated wherein the reported obstructive sleep apnea event is shorter than the detection window and overlaps at least in part with the detection window.

2. The apparatus of claim 1, wherein determining that obstructive sleep apnea is indicated comprises smoothing measures of the cyclic variation in heart rate over the detection window, wherein smoothing the measures of the cyclic variation in heart rate reduces the variability between the measures for consecutive and/or proximate time intervals.

3. The apparatus of claim 2, wherein reporting the obstructive sleep apnea event comprises reporting information characterizing an aspect of the physiological condition of the monitored individual outside of the detection window.

4. The apparatus of claim 1, wherein reporting the obstructive sleep apnea event comprises transmitting information characterizing an aspect of the physiological condition of the monitored individual to a remote medical receiver.

5. The apparatus of claim 1, wherein reporting the obstructive sleep apnea event comprises reporting information characterizing aspects of the physiological condition of the monitored individual other than the heart.

6. The apparatus of claim 1, wherein the reported obstructive sleep apnea event begins before the detection window or ends after the detection window.

7. The apparatus of claim 1, wherein the reporting of the obstructive sleep apnea event characterizes the heart rate of an individual at different times during the obstructive sleep apnea event.

8. The apparatus of claim 1, wherein the reporting of the obstructive sleep apnea event characterizes the frequency of the cyclic variation in heart rate during the obstructive sleep apnea event.

9. A machine-implemented method comprising:
analyzing a heart rate series of a monitored individual in the time domain using one or more digital data processing devices, the time domain analysis establishing whether one or more indices of cyclic variation in heart rate are present in the heart rate series;
establishing whether one or more indices of tachycardia are present in the heart rate series;
establishing whether one or more indices of bradycardia are present in the heart rate series;
individually scoring the tachycardia indices, the bradycardia indices, and the cyclic variation in heart rate indices;
collectively scoring the tachycardia indices, the bradycardia indices, and the cyclic variation in heart rate indices;
determining whether a sleep disorder is indicated based on at least one of the individual scoring and the collective scoring; and
outputting, over an output, a report characterizing a sleep disorder event based on the determination of whether the sleep disorder is indicated.

10. The method of claim 9, wherein determining whether the sleep disorder is indicated comprises determining that periodic limb movement sleep disorders are indicated based on tachycardia indices indicating that tachycardia is present, bradycardia indices indicating that bradycardia is not present, and cyclic variation in heart rate indices indicating that cyclic variation in heart rate is present.

11. The method of claim 9, wherein determining whether the sleep disorder is indicated comprises determining that obstructive sleep apneas are indicated based on tachycardia indices indicating that tachycardia is not present, bradycardia indices indicating that bradycardia is present, and cyclic variation in heart rate indices indicating that cyclic variation in heart rate is present.

12. The method of claim 9, wherein determining whether the sleep disorder is indicated comprises determining that repeated central apneas or Cheyne-Stokes respiration are indicated based on tachycardia indices indicating that tachycardia is present, bradycardia indices indicating that bradycardia is present, and cyclic variation in heart rate indices indicating that cyclic variation in heart rate is present.

13. The method of claim 9, wherein determining whether the sleep disorder is indicated comprises determining that repeated central apneas or Cheyne-Stokes respiration are indicated based on tachycardia indices indicating that tachycardia is not present, bradycardia indices indicating that bradycardia is not present, and cyclic variation in heart rate indices indicating that cyclic variation in heart rate is present.

14. The method of claim 9, further comprising progressively lowering thresholds for one or more of the cyclic variation in heart rate indices, the tachycardia indices, and the bradycardia indices until one of periodic limb movement sleep disorders, obstructive sleep apneas, or repeated central apneas or Cheyne-Stokes respiration is indicated.

15. The method of claim 9, wherein analyzing the heart rate series comprises autocorrelating the heart rate series.

16. The method of claim 15, wherein detecting the cyclic variation in heart rate comprises scoring autocorrelation measures to characterize a likelihood that the autocorrelation measures indicate a sleep disorder, wherein the measures include a number of zero crossings of an autocorrelated heart rate series, distances between adjacent zero crossings, and a standard deviation of the distances between adjacent zero crossings.

17. The method of claim 16, wherein the measures further include a measure f given by:

$$f = \frac{1000}{L*mRR}$$

where L is the mean distance between the adjacent zero crossings over a time interval and mRR is the mean RR interval over a time interval.

18. The method of claim 16, wherein detecting the cyclic variation in heart rate further comprises scoring measures of the heart rate series to characterize the likelihood that the heart rate series measures are indicative of a sleep disorder.

19. The method of claim 9, wherein reporting the sleep disorder event comprises reporting information characterizing aspects of the physiological condition of the monitored individual other than the heart.

20. The method of claim 9, wherein reporting the sleep disorder event comprises reporting information characterizing movement of a part of the body other than the heart.

21. The method of claim 9, wherein reporting the sleep disorder event comprises reporting an obstructive sleep apnea event based exclusively on the detection of the cyclic variation in heart rate in the heart rate series.

22. The method of claim 9, wherein the indices of bradycardia include a number of decreases below a baseline heart rate within a longer interval.

23. The method of claim 9, wherein the indices of tachycardia include a number of increases above a baseline heart rate within a longer interval.

24. A system comprising:
an electrocardiograph configured to generate an electrocardiogram of a monitored individual;
a data processing device programmed to detect an obstructive sleep apnea disorder event of the monitored individual based exclusively on the electrocardiogram;
one or more machine-readable data storage media storing instructions operable to cause the data processing device to perform operations to detect the obstructive sleep apnea disorder event of the monitored individual, the operations comprising receiving, in the electrocardiogram, machine-readable heart rate information characterizing a heart rate of the monitored individual over a detection window, determining a quantity of bradycardia events present in at least a portion of the received heart rate information, wherein the determining comprises:

deciding that a bradycardia event has occurred when at least one of the following is true: (i) the heart rate of the monitored individual is below a predetermined threshold and (ii) the heart rate of the monitored individual is below a baseline heart rate derived from at least a portion of the received heart rate information;

detecting a cyclic variation in the received heart rate information;

determining that obstructive sleep apnea is indicated over the detection window based on a combined analysis of the number of bradycardia events present in the received heart rate information and the detected cyclic variation in the received heart rate information; and selectively and individually reporting in real time the obstructive sleep apnea disorder event in response to the determination that sleep apnea is indicated, wherein the reported obstructive sleep apnea event is shorter than the detection window and overlaps at least in part with the detection window; and a transmitter configured to report information characterizing the physiological condition of the monitored individual during the detected obstructive sleep apnea disorder event.

25. The system of claim 24, wherein the data processing device is configured to detect the obstructive sleep apnea disorder event by analyzing a heart rate series derived from the electrocardiogram in the time domain.

26. The system of claim 25, wherein the data processing device comprises an autocorrelator configured to cross correlate the heart rate series with itself.

27. The system of claim 26, wherein the data processing device further comprises a scoring unit to score measures of the autocorrelation of the heart rate series to characterize the likelihood that the autocorrelation measures are indicative of the obstructive sleep apnea disorder event.

28. The system of claim 27, wherein the autocorrelation measures include a number of zero crossings of an autocorrelated heart rate series, distances between adjacent zero crossings, and a standard deviation of the distances between adjacent zero crossings.

29. The system of claim 27, wherein the autocorrelation measures include a measure f given by:

$$f = \frac{1000}{L*mRR}$$

where L is the mean distance between adjacent zero crossings of an autocorrelated heart rate series over a time interval and mRR is the mean RR interval over a time interval.

30. The system of claim 26, wherein the scoring unit also scores measures of the heart rate series to characterize the likelihood that the heart rate series measures are indicative of the obstructive sleep apnea event.

31. The system of claim 24, wherein the system further comprises one or more additional monitoring devices configured to generate information characterizing aspects of the physiological condition of a monitored individual other than activity of the heart.

32. The system of claim 31, wherein the transmitter is also configured to report the information generated by the additional monitoring devices.

33. The system of claim 24, wherein the system further comprises a beat detector.

34. The system of claim 24, wherein the electrocardiograph comprises a patient portable sensing unit.

* * * * *